(12) United States Patent
Merkel et al.

(10) Patent No.: US 10,000,431 B1
(45) Date of Patent: Jun. 19, 2018

(54) PROCESS FOR THE PRODUCTION OF 1-CHLORO-3,3,3-TRIFLUOROPROPENE (HCFO-1233ZD)

(71) Applicant: Honeywell International Inc., Morris Plains, NJ (US)

(72) Inventors: Daniel C. Merkel, Orchard Park, NY (US); Hsueh Sung Tung, Getzville, NY (US)

(73) Assignee: Honeywell International Inc., Morris Plains, NJ (US)

( * ) Notice: Subject to any disclaimer, the term of this patent is extended or adjusted under 35 U.S.C. 154(b) by 0 days. days.

(21) Appl. No.: 15/883,541

(22) Filed: Jan. 30, 2018

(51) Int. Cl.
C07C 17/25 (2006.01)
C07C 17/20 (2006.01)
C07C 17/383 (2006.01)

(52) U.S. Cl.
CPC ............ *C07C 17/206* (2013.01); *C07C 17/25* (2013.01); *C07C 17/383* (2013.01)

(58) Field of Classification Search
CPC ............................... C07C 17/25; C07C 17/206
See application file for complete search history.

(56) References Cited

U.S. PATENT DOCUMENTS

| | | | |
|---|---|---|---|
| 6,166,274 A | 12/2000 | Chen et al. | |
| 6,844,475 B1 | 1/2005 | Tung et al. | |
| 7,829,747 B2 | 11/2010 | Wang et al. | |
| 8,202,617 B2 | 6/2012 | Kitahara et al. | |
| 8,217,208 B2 | 7/2012 | Hulse et al. | |
| 8,618,338 B2 | 12/2013 | Elsheikh et al. | |
| 8,704,017 B2 | 4/2014 | Pokrovski et al. | |
| 8,779,218 B2 | 7/2014 | Pigamo et al. | |
| 8,835,700 B2 | 9/2014 | Pokrovski et al. | |
| 8,921,621 B2 | 12/2014 | Cottrell et al. | |
| 9,018,430 B2 | 4/2015 | Merkel et al. | |
| 9,024,092 B2 | 5/2015 | Merkel et al. | |
| 9,045,386 B2 | 6/2015 | Tung et al. | |
| 9,102,579 B2 | 8/2015 | Light et al. | |
| 9,102,580 B2 | 8/2015 | Nappa et al. | |
| 9,328,043 B2 | 5/2016 | Wang et al. | |
| 9,334,206 B2 | 5/2016 | Wang et al. | |
| 2016/0332936 A1 | 11/2016 | Wang et al. | |

FOREIGN PATENT DOCUMENTS

JP 2017124997 A 7/2017
WO 2016009946 A1 1/2016

OTHER PUBLICATIONS

WO2016009946 (A1), Jan. 21, 2016, pp. 1-15; English translation (Year: 2016).*

* cited by examiner

*Primary Examiner* — Medhanit W Bahta
(74) *Attorney, Agent, or Firm* — Faegre Baker Daniels LLP

(57) ABSTRACT

A process for enhancing the selective and efficient production of (E)-1-chloro-3,3,3-trifluoropropene (HCFO-1233zd (E), or 1233zd(E)). During the manufacture of HCFO-1233zd(E) by fluorination of 1,1,1,3,3-pentachloropropane (HCC-240fa), a by-product of 1,1,3,3-tetrachloro-1-fluoropropane (HCFC-241fa) is separated and then dehydrochlorinated to form 1,3,3-trichloro-3-fluoropropene (HCFO-1231zd). The HCFO-1231zd is then fluorinated to form HCFO-1233zd(E).

19 Claims, 13 Drawing Sheets

Fig. 11

Comparison of HCC-240fa, HCFC-241fa, and HCFO-1231zd feedstocks to make HCFO-1233zd (140°C and 1 hour hold time)

| Exp# | Temp (oC) | HF charged (g) | HF charged (mol) | 240fa charged (g) | 240fa charged (mol) | HF:240fa mole ratio | Hold time (hr) | 240fa conv (%) |
|---|---|---|---|---|---|---|---|---|
| 1 | 140 | 84.4 | 4.2 | 53.4 | 0.2 | 17.1 | 1 | 99.5 |

By-Product Selectivities (mol%)

| TFPy | 1234ze(E) | 1234ze(Z) | 245fa | 1233zd(E) | 1233zd(Z) | 244fa | 1233zd(Z) | 243 iso's | 242 iso's | 241 iso | others |
|---|---|---|---|---|---|---|---|---|---|---|---|
| 0.41 | 0 | 0.06 | 5.29 | 66.30 | 1.91 | 3.96 | 0.97 | 1.14 | 19.10 | 0.86 |

| Exp# | Temp (oC) | HF charged (g) | HF charged (mol) | 241fa charged (g) | 241fa charged (mol) | HF:241fa mole ratio | Hold time (hr) | 241fa conv (%) |
|---|---|---|---|---|---|---|---|---|
| 2 | 140.0 | 89.7 | 4.5 | 53.4 | 0.3 | 16.8 | 1 | 51.4 |

By-Product Selectivities (mol%)

| TFPy | 1234ze(E) | 1234ze(Z) | 245fa | 1233zd(E) | 1233zd(Z) | 244fa | 1233zd(Z) | 243 iso's | 242 iso's | 241 iso | others |
|---|---|---|---|---|---|---|---|---|---|---|---|
| 0.34 | 0.98 | 0.21 | 14.43 | 64.47 | 0.24 | 3.88 | 0.42 | 10.95 | 0.23 | 3.86 |

| Exp# | Temp (oC) | HF charged (g) | HF charged (mol) | 1231zd charged (g) | 1231zd charged (mol) | HF:1231zd mole ratio | Hold time (hr) | 1231zd conv (%) |
|---|---|---|---|---|---|---|---|---|
| 3 | 140 | 91.2 | 4.6 | 43.3 | 0.27 | 17.2 | 1.0 | 99.6 |

By-Product Selectivities (mol%)

| TFPy | 1234ze(E) | 1234ze(Z) | 245fa | 1233zd(E) | 1233zd(Z) | 244fa | 1233zd(Z) | 243 iso's | 242 iso's | 241 iso | others |
|---|---|---|---|---|---|---|---|---|---|---|---|
| 0.02 | 0.23 | 0.04 | 0.47 | 88.79 | 0.23 | 4.53 | 3.86 | 0.41 | 1.41 | 1.86 |

Fig. 12

Comparison of HCC-240fa, HCFC-241fa, and HCFO-1231zd feedstocks to make HCFO-1233zd
(130°C and 3 hour hold time)

| Exp# | Temp (oC) | HF charged (g) | HF charged (mol) | 240fa charged (g) | 240fa charged (mol) | HF:240fa mole ratio | Hold time (hr) | 240fa conv (%) |
|---|---|---|---|---|---|---|---|---|
| 4 | 130 | 85.2 | 4.3 | 53.2 | 0.2 | 17.3 | 3 | 99.5 |

| | | | | By-Product Selectivities (mol%) | | | | |
|---|---|---|---|---|---|---|---|---|
| TFPy | 1234ze(E) | 245fa | 1234ze(Z) | 1233zd(E) | 244fa | 1233zd(Z) | 243 iso's | 242 iso's | 241 iso | others |
| 0.02 | 0 | 3.23 | 0.06 | 77.01 | 0.40 | 4.73 | 0.83 | 2.78 | 10.15 | 0.46 |

| Exp# | Temp (oC) | HF charged (g) | HF charged (mol) | 241fa charged (g) | 241fa charged (mol) | HF:241fa mole ratio | Hold time (hr) | 241fa conv (%) |
|---|---|---|---|---|---|---|---|---|
| 5 | 130.0 | 91.3 | 4.6 | 52.5 | 0.3 | 17.4 | 3 | 84.3 |

| | | | | By-Product Selectivities (mol%) | | | | |
|---|---|---|---|---|---|---|---|---|
| TFPy | 1234ze(E) | 245fa | 1234ze(Z) | 1233zd(E) | 244fa | 1233zd(Z) | 243 iso's | 242 iso's | 241 iso | others |
| 0.01 | 0.49 | 4.57 | 0.28 | 83.35 | 0.22 | 4.73 | 0.57 | 5.14 | 0.00 | 0.63 |

| Exp# | Temp (oC) | HF charged (g) | HF charged (mol) | 1231zd charged (g) | 1231zd charged (mol) | HF:1231zd mole ratio | Hold time (hr) | 1231zd conv (%) |
|---|---|---|---|---|---|---|---|---|
| 6 | 130 | 90.7 | 4.5 | 45.6 | 0.28 | 16.2 | 3.0 | 99.7 |

| | | | | By-Product Selectivities (mol%) | | | | |
|---|---|---|---|---|---|---|---|---|
| TFPy | 1234ze(E) | 245fa | 1234ze(Z) | 1233zd(E) | 244fa | 1233zd(Z) | 243 iso's | 242 iso's | 241 iso | others |
| 0.01 | 0.27 | 0.38 | 0.07 | 87.53 | 0.73 | 4.94 | 5.29 | 0.53 | 0.19 | 2.45 |

Fig. 13

Comparison of HCFC-241fa, and HCFO-1231zd feedstocks to make HCFO-1233zd (130°C and 1 hour hold time)

| Exp# | Temp (oC) | HF charged (g) | HF charged (mol) | 241fa charged (g) | 241fa charged (mol) | HF:241fa mole ratio | Hold time (hr) | 241fa conv (%) |
|---|---|---|---|---|---|---|---|---|
| 7 | 130.0 | 89.2 | 4.5 | 50.9 | 0.3 | 17.5 | 1 | 51.8 |

By-Product Selectivities (mol%)

| TFPy | 1234ze(E) | 1234ze(Z) | 245fa | 1233zd(E) | 244fa | 1233zd(Z) | 243 iso's | 242 iso's | 241 iso | others |
|---|---|---|---|---|---|---|---|---|---|---|
| 0.12 | 1.03 | 0.22 | 10.33 | 72.68 | 0.21 | 3.94 | 2.07 | 7.17 | 0.19 | 2.04 |

| Exp# | Temp (oC) | HF charged (g) | HF charged (mol) | 1231zd charged (g) | 1231zd charged (mol) | HF:1231zd mole ratio | Hold time (hr) | 1231zd conv (%) |
|---|---|---|---|---|---|---|---|---|
| 8 | 130 | 90.3 | 4.5 | 41.8 | 0.26 | 17.6 | 1.0 | 99.6 |

By-Product Selectivities (mol%)

| TFPy | 1234ze(E) | 1234ze(Z) | 245fa | 1233zd(E) | 244fa | 1233zd(Z) | 243 iso's | 242 iso's | 241 iso | others |
|---|---|---|---|---|---|---|---|---|---|---|
| 0.00 | 0.16 | 0.03 | 0.19 | 90.03 | 0.21 | 3.71 | 5.28 | 0.16 | 0.22 | 0.83 |

PROCESS FOR THE PRODUCTION OF 1-CHLORO-3,3,3-TRIFLUOROPROPENE (HCFO-1233ZD)

BACKGROUND

1. Field of the Disclosure

The present disclosure relates to a process for enhancing the selective and efficient production of 1-chloro-3,3,3-trifluoropropene (HCFO-1233zd, or 1233zd) and, in particular, to a process for enhancing the selective and efficient production of HCFO-1233zd(E).

2. Description of the Related Art

Fluorocarbon based fluids have found widespread use in industry in a number of applications, including use as refrigerants, aerosol propellants, blowing agents, heat transfer media, and gaseous dielectrics. Due to suspected environmental problems associated with the use of some of these fluids, including the relatively high global warming potentials associated therewith, it is desirable to use fluids having the lowest possible global warming potential (GWP) in addition to also having zero ozone depletion potential (ODP). Thus, there is considerable interest in developing environmentally friendlier materials for various applications, such as those mentioned above.

Hydrochlorofluoroolefins (HCFOs) having zero ozone depletion and low global warming potential have been identified as potentially filling this need. However, the toxicity, boiling point, and other physical properties of such chemicals vary greatly from isomer to isomer. One HCFO having valuable properties is (E)-1-chloro-3,3,3-trifluoropropene (HCFO-1233zd(E)), which has been proposed as a next generation non ozone depleting and low global warming potential solvent.

(E)-1-chloro-3,3,3-trifluoropropene (HCFO-1233zd(E), or 1233zd(E)) is a new Low Global Warming and Non-Ozone Depleting molecule, which has applications as a blowing agent, solvent, and refrigerant. The applications and interest in this molecule have resulted in the development of several manufacturing processes for its production.

In one commercial process, HCFO-1233zd(E) is produced by fluorination of 1,1,1,3,3-pentachloropropane (HCC-240fa) using hydrofluoric acid (HF). However, in this process, various by-products are formed, such as 1,1,3,3-tetrachloro-1-fluoropropane (HCFC-241fa), which compromise the selectivity and efficiency of the production of HCFO-1233zd(E).

What is needed is an improved method for the production of HCFO-1233zd(E).

SUMMARY

The present disclosure relates to a process for enhancing the selective and efficient production of (E)-1-chloro-3,3,3-trifluoropropene (HCFO-1233zd(E), or 1233zd(E)). During the manufacture of HCFO-1233zd(E) by fluorination of 1,1,1,3,3-pentachloropropane (HCC-240fa), a by-product of 1,1,3,3-tetrachloro-1-fluoropropane (HCFC-241fa) is separated and then dehydrochlorinated to form 1,3,3-trichloro-3-fluoropropene (HCFO-1231zd). The HCFO-1231zd is then fluorinated to form HCFO-1233zd(E).

In one form thereof, the present disclosure provides a process for the production of 1-chloro-3,3,3-trifluoropropene (HCFO-1233zd), including the steps of: providing a reactant composition including 1,1,3,3-tetrachloro-1-fluoropropane (HCFC-241fa); dehydrochlorinating the HCFC-241fa in the presence of a basic solution to form 1,3,3-trichloro-3-fluoropropene (HCFO-1231zd); and fluorinating the HCFO-1231zd with hydrogen fluoride (HF) to produce HCFO-1233zd.

Following the fluorinating step, the HCFO-1233zd produced may be predominantly HCFO-1233zd(E). The dehydrochlorinating step may be performed at a temperature between 0° C. and 100° C.

The fluorinating step may be performed at a temperature between 80° C. and 150° C. The fluorinating step may be performed in the absence of a catalyst.

The reactant composition may further include hydrogen fluoride (HF) and the process may further include the additional step, after the providing step and prior to the dehydrochlorinating step, of separating HF from the reactant composition.

The process may further include the additional step, after the dehydrochlorinating step and prior to the fluorinating step, of drying the HCFO-1231zd.

The basic solution in the dehydrochlorinating step may be selected from the group consisting of potassium hydroxide (KOH), sodium hydroxide (NaOH), and calcium hydroxide (CaOH).

In another form thereof, the present disclosure provides a process for the production of 1-chloro-3,3,3-trifluoropropene (HCFO-1233zd), including the steps of: fluorinating 1,1,1,3,3-pentachloropropane (HCC-240fa) with hydrofluoric acid (HF) to produce a product stream including HCFO-1233zd and 1,1,3,3-tetrachloro-1-fluoropropane (HCFC-241fa); separating HCFC-241fa from the product stream; dehydrochlorinating the HCFC-241fa in a liquid phase in the presence of a basic solution to form 1,3,3-trichloro-3-fluoropropene (HCFO-1231zd); and fluorinating the HCFO-1231zd with hydrogen fluoride (HF) to produce HCFO-1233zd.

The first fluorinating step may be performed at a reaction temperature between 120° C. and 140° C. and at a reaction pressure of between 230 psig and 400 psig.

Following the second fluorinating step, the HCFO-1233zd produced may be predominantly HCFO-1233zd(E). The dehydrochlorinating step may be performed at a temperature between 0° C. and 100° C.

The second fluorinating step may be performed at a temperature between 80° C. and 150° C. The second fluorinating step may be performed in the absence of a catalyst.

The reactant composition may further include hydrogen fluoride (HF) and the process may further include the additional step, after the first fluorinating step and prior to the dehydrochlorinating step, of separating HF from the product stream.

The process may further include the additional step, after the dehydrochlorinating step and prior to the second fluorinating step, of drying the HCFO-1231zd. The process may further include the additional step, after the second fluorinating step, of recycling at least one of unreacted HCFO-1231zd and unreacted HF back to the first fluorinating step.

The separating step may be conducted via vacuum distillation. The separating step may be conducted via distillation at a pressure between 10 torr and 5,200 torr.

The above mentioned and other features of the disclosure, and the manner of attaining them, will become more apparent and the disclosure itself will be better understood by reference to the following description of embodiments of the disclosure taken in conjunction with the accompanying drawings.

BRIEF DESCRIPTION OF THE DRAWINGS

The above mentioned and other features of the disclosure, and the manner of attaining them, will become more apparent and the disclosure itself will be better understood by reference to the following description of embodiments of the disclosure taken in conjunction with the accompanying drawings.

FIG. 11 corresponds to Example 5, and is a table showing a comparison of HCC-240fa, HCFC-241fa, and HCFO-1231zd feedstocks to make HCFO-1233zd (140° C. and 1 hour hold time);

FIG. 12 corresponds to Example 5, and is a table showing a comparison of HCC-240fa, HCFC-241fa, and HCFO-1231zd feedstocks to make HCFO-1233zd (130° C. and 3 hour hold time); and FIG. 13 corresponds to Example 5, and is a table showing a comparison of HCFC-241fa, and HCFO-1231zd feedstocks to make HCFO-1233zd (130° C. and 1 hour hold time).

Figure 1:
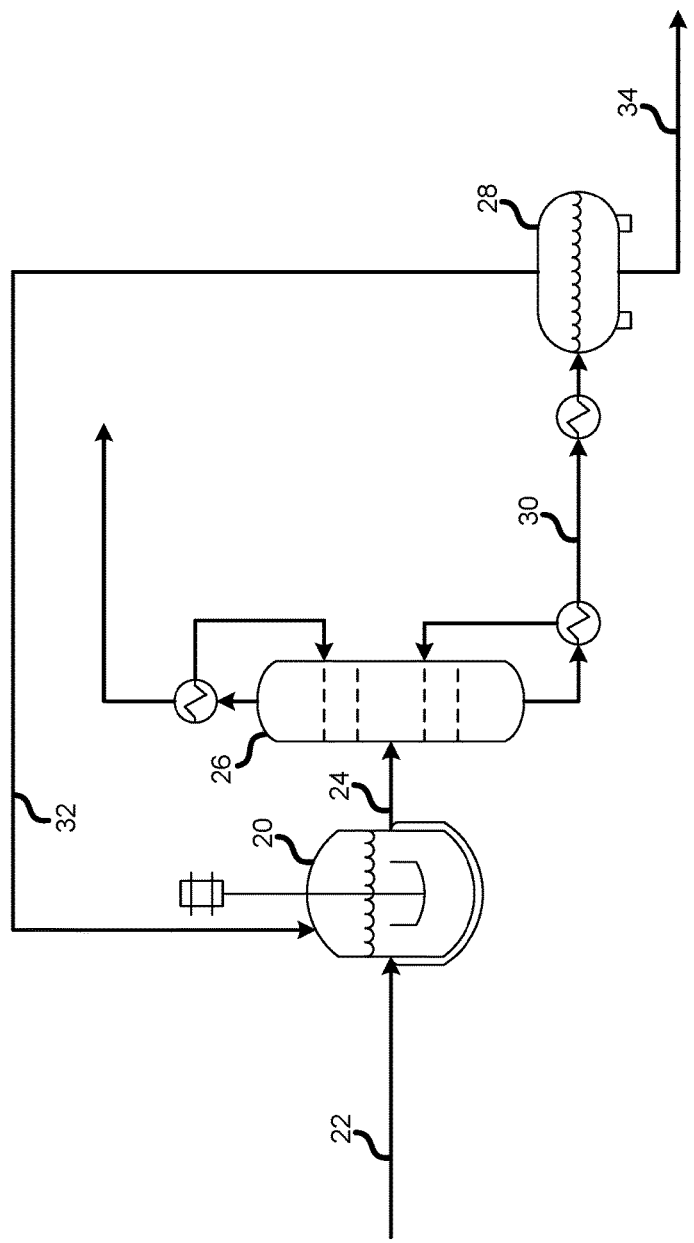
FIG. 1 is a schematic diagram of the first step of the present process according to a first embodiment.

Corresponding reference characters indicate corresponding parts throughout the several views. Although the drawings represent embodiments of various features and components according to the present disclosure, the drawings are not necessarily to scale and certain features may be exaggerated in order to better illustrate and explain the present disclosure. The exemplification set out herein illustrates an embodiment of the disclosure, and such exemplification is not to be construed as limiting the scope of the disclosure in any manner.

DETAILED DESCRIPTION

The present disclosure relates to a process for enhancing the selective and efficient production of (E)-1-chloro-3,3,3-trifluoropropene (HCFO-1233zd(E), or 1233zd(E)). During the manufacture of HCFO-1233zd(E) by fluorination of 1,1,1,3,3-pentachloropropane (HCC-240fa), a by-product of 1,1,3,3-tetrachloro-1-fluoropropane (HCFC-241fa) is separated and then dehydrochlorinated to form 1,3,3-trichloro-3-fluoropropene (HCFO-1231zd). The HCFO-1231zd is then fluorinated to form HCFO-1233zd(E).

I. Background

The overall chemical equation for the non-catalytic reaction of HCC-240fa and hydrogen fluoride (HF) to form 1-chloro-3,3,3-trifluoropropene (HCFO-1233zd) is set forth below as Equation (I):

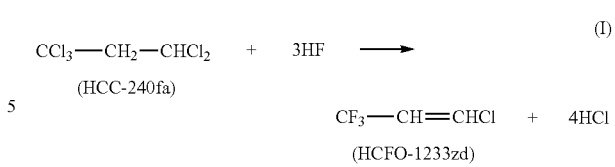

Typically, the foregoing reaction is performed without a catalyst in an agitated liquid phase reactor at a reaction temperature of 120-140° C. and a reaction pressure of 230-400 psig.

It is believed that the foregoing overall reaction has two distinct reaction pathways, including a desired pathway, set forth below in Equation (II), and a competing pathway, set forth below in Equation (III):

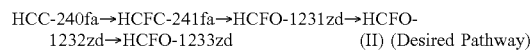

In the desired pathway of Equation (II), HCC-240fa is converted to 1,1,3,3-tetrachloro-1-fluoropropane (HCFC-241fa), which is then converted to 1,3,3-trichloro-3-fluoropropene (HCFO-1231zd), which is then converted to 1,3-chloro-3,3-difluoropropene (HCFO-1232zd), which is then converted to HCFO-1233zd.

However, in the competing pathway of Equation (III), HCC-240fa is converted to HCFC-241fa, and then to 1,3,3,-trichloro-1,1-difluoropropane (HCFC-242fa), which disadvantageously will not react further to form HCFO-1233zd but rather will react to form various isomers of 1,2-dichloro-3,3,3-trifluoropropane (HCFC-243).

It has been found that the desired pathway of Equation (II), which includes the saturated intermediate HCFC-241fa, has an overall relatively low selectivity of only about 65% to HCFO-1233zd. It is believed that the low selectivity can mostly be attributed to the formation of the saturated by-product HCFC-242fa via the non-catalytic reaction of HCFC-241fa with anhydrous HF under the foregoing reaction conditions according to the competing pathway of Equation (III).

It has also been established experimentally by the present inventors that HCFC-242fa conversion to HCFO-1233zd in the presence of anhydrous HF under the foregoing non-catalytic reaction conditions is very low (<5%), such that HCFC-242fa is essentially unreactive in producing HCFO-1233zd under the foregoing non-catalytic reaction conditions. In particular, in the desired pathway of Equation (II) above, the slowest reaction rate, or rate determining step, is the reaction of HCFC-241fa to HCFO-1231zd. Unfortunately however, the competing reaction of HCFC-241fa to HCFC-242fa according to the competing pathway of Equation (III) also occurs, with the HCFC-242fa produced being very stable and essentially unreactive to yield HCFO-1233zd. The slow reaction rate of HCFC-241fa to HCFO-1231zd therefore provides ample time for the competing reaction to occur, wherein the overall selectivity to HCFO-1233zd according to the desired pathway of Equation (II) above is only about 75-85%.

This can be seen in a gas chromatography (GC) analysis of the HCFO-1233zd crude product that is produced by the foregoing non-catalytic process, wherein analysis shows that the major component of all of the high boiling point by-products of HCFO-1233zd which are produced in the process is HCFC-242fa.

In Table I below, an exemplary average composition is set forth of a HCFO-1233zd crude product stream from a continuous non-catalytic process performed under the foregoing reaction conditions downstream of a recycle column which returns a bottoms stream containing the majority of the unreacted anhydrous HF and HCC-240fa, and intermediates HCFO-1231zd, HCFO-1232zd, and HCFC-241fa back to the reactor for further conversion, as discussed below.

In Table I below, high boiling by-products are set forth in boldface.

TABLE I

| Component | Wt. % |
|---|---|
| HF | 1.9 |
| HFC-245fa | 0.14 |
| HFO-1234ze isomer 1 | 0.69 |
| HFO-1234ze isomer 2 | 0.20 |
| HCFC-244fa | 0.74 |
| HCFO-1233zd isomers | 79.46 |
| HCFC-243 isomers | 2.06 |
| HCFC-242fa | 13.44 |
| HCFC-242fb | 0.32 |
| HCFC-241 isomer | 0.73 |
| HCFO-1232 isomers | 0.04 |
| Others | 0.29 |

II. Overview of the Present Process.

According to the present process, HCFC-241fa produced in the HCC-240fa reaction of Equation (II) is first separated or isolated, and is then dehydrochlorinated in the presence of a basic solution, such as a solution of potassium hydroxide (KOH), to form HCFO-1231zd according to Equation (IV) below:

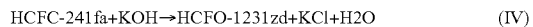

$$\text{HCFC-241fa} + \text{KOH} \rightarrow \text{HCFO-1231zd} + \text{KCl} + \text{H}_2\text{O} \quad \text{(IV)}$$

Then, the HCFO-1231zd formed may be introduced into a non-catalytic reactor, either by itself, or optionally, in combination with HCC-240fa. Advantageously, the HCFO-1231zd will react very quickly via a fluorination reaction with hydrogen fluoride to form the desired end product HCFO-1233zd with high selectivity according to Equation (V) below:

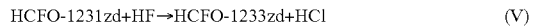

$$\text{HCFO-1231zd} + \text{HF} \rightarrow \text{HCFO-1233zd} + \text{HCl} \quad \text{(V)}$$

In this manner, in order to avoid the yield loss from producing HCFO-242fa from HCFC-241fa, the present process increases the yield of the non-catalytic HCFO-1233zd process by first converting the HCFC-241fa with high yield to an unsaturated hydrochlorofluoro-olefin (HCFO), namely HCFO-1231zd, by dehydrochlorination. The HCFO-1231zd in turn reacts readily with hydrogen fluoride in the absence of a catalyst to form HCFO-1233zd in good yield. The present method therefore improves the overall yield of the main HCFO-1233zd non-catalytic process by converting a major by-product of that process, HCFC-241fa, into an intermediate HCFO-1231zd that in turn reacts readily to the desired HCFO-1233zd product.

The first step of the present process is to separate, or isolate, a HCFC-241fa crude by-product stream from the main reaction in which HCC-240fa is reacted with hydrogen fluoride (HF) to form HCFO-1233zd. This can be readily accomplished by removing the majority of the HF by employing a phase separator due to the fact that HF and HCFC-241fa are immiscible and can be readily separated in a phase separator by virtue of their differences in density. Further, cooling the mixture of HF and HCFC-241fa, such as to less than 10° C. or cooler, for example, enhances the separation. The less dense or upper HF phase may be recycled back to the non-catalytic fluorination reactor for further processing. As discussed in detail below, the more dense or lower HCFC-241fa crude phase, typically containing less than 5 wt. % HF after the foregoing separation, may then be fed directly to the second step of the present process. The amount of HF remaining in the HCFC-241fa crude phase is typically less than 5 wt. %, less than 3 wt. %, or less than 2 wt. %, for example.

Relatively pure HCFC-241fa may then be isolated using additional batch or continuous distillation, which may be run under vacuum or at pressure. Vacuum distillation may improve the separation by one or more of the following attributes: (1) prevention of product degradation because of reduced pressure leading to lower distillation column bottoms temperatures, (2) reduction of product degradation because of reduced mean residence time, especially in columns using packing rather than trays, and (3) increasing capacity, yield, and purity. Another advantage of vacuum distillation is the reduced capital cost, at the expense of slightly more operating cost. Utilizing vacuum distillation may reduce the height and diameter, and thus the capital cost, of a distillation column.

Typically, this distillation may be run at pressures as little as 10 torr, 100 torr, or 500 torr, or as great as 1,000 torr, 2,500 torr, or 5,200 torr, or within any range defined between any pair of the foregoing values, such as 10 to 5,200 torr, 100 to 2,500 torr, or 500 to 1,000 torr, for example.

In another embodiment, the remaining HF may be removed from the HCFC-241fa crude stream by washing with water or with a weak basic solution. In a still further embodiment, the HCFC-241fa may come from another source, such as purposely producing HCFC-241fa from HCFC-240fa or a tetrachloropropene, or by purchasing HCFC-241fa.

The second step of the present process is the conversion of HCFC-241fa to 1,3,3-trichloro-3-fluoropropene (HCFO-1231zd) by dehydrochlorination using a basic solution, such as a 1-50 wt. % basic solution, for example, according to Equation (IV) above. Of note, this step may be considered the first step of the present process if HCFC-241fa is obtained from an alternative source per the preceding paragraph.

The basic solution may include one or more of potassium hydroxide (KOH), sodium hydroxide (NaOH), calcium hydroxide (CaOH), or any other alkali earth metal or alkali metal hydroxide. The foregoing reaction may be performed in an agitated liquid phase reactor at a reaction pressure of 500 torr to 3300 torr. The reaction may be run at relatively low temperatures as little as 0° C., 25° C., or 40° C., or at temperatures as high as 60° C., 75° C., or 100° C., or within any range defined between any two of the foregoing values, such as 0° C. to 100° C., 25° C. to 75° C., or 40° C. to 60° C., for example. The selectivity to HCFO-1231zd in an experimental reaction was greater than 83.5%.

The HCFO-1231zd crude stream is then phase separated by density difference and then may then be dried using a desiccant such as molecular sieves, calcium sulfate, magnesium sulfate, sulfuric acid, or silica gel, for example.

Similar to the first step, relatively pure HCFO-1231zd may then be isolated using additional batch or continuous distillation, which may be run under vacuum or at pressure. Vacuum distillation may improve the separation by one or more of the following attributes: (1) prevention of product degradation because of reduced pressure leading to lower distillation column bottoms temperatures, (2) reduction of product degradation because of reduced mean residence time, especially in columns using packing rather than trays, and (3) increasing capacity, yield, and purity. Another advantage of vacuum distillation is the reduced capital cost, at the expense of slightly more operating cost. Utilizing vacuum distillation may reduce the height and diameter, and thus the capital cost, of a distillation column.

Typically, this distillation may be run at pressures as little as 10 torr, 100 torr, or 500 torr, or as great as 1,000 torr, 2,500 torr, or 5,200 torr, or within any range defined between any pair of the foregong values, such as 10 to 5,200 torr, 100 to 2,500 torr, or 500 to 1,000 torr, for example.

In the third step of the present process, the dried HCFO-1231zd crude stream is fed to a fluorination reactor where the HCFO-1231zd crude stream is fluorinated to form the desired HCFO-1233zd product according to Equation (V) above. The reactor may be an agitated liquid phase fluorination reactor, for example. Further, the reactor may be the same reactor used for the fluorination of HCFC-240fa, or the reactor may be a dedicated, stand-alone reactor used only for the fluorination of the HCFO-1231zd crude stream to form the desired HCFO-1233zd product. The fluorination reaction may be performed at temperatures as little as 50° C., 80° C., or 100° C., or as high as 125° C., 150° C., or 200° C., or within any range defined between any two of the foregoing values, such as 50° C. to 200° C., 80° C. to 150° C., or 100° C. to 125° C., for example. The fluorination reaction may be performed at a reaction pressure as little as 100 psig or 200 psig or as great as 350 psig or 500 psig, or within any range defined between any two of the foregoing values, such as 100 to 500 psig or 200 to 350 psig, for example. Suitable HF to HCFO-1231zd ratios for the fluorination reaction may be as little as 2:1, 5:1, or 10:1, or as great as 50:1, 75:1, or 100:1, or within any range defined between any two of the foregoing values, such as 2:1 to 100:1, 5:1 to 75:1, or 10:1 to 50:1, for example. It has been found that fluorination of HCFO-1231zd with anhydrous HF at 80-150° C. produces HCFO-1233zd(E) with a relatively high conversion of greater than 95% and a relatively high selectivity of greater than 90%. Unreacted anhydrous HF and unreacted HCFO-1231zd, and/or any HCFO-1232zd intermediate which may be formed, may be recycled back to the reactor for further processing.

The HCFO-1233zd crude product may be purified by conventional techniques such as distillation or scrubbing/drying to remove the HCl co-product, phase separation and/or scrubbing/drying to remove any residual HF and/or moisture, and distillation to remove any organic impurities. The HCFO-1233zd may be predominantly HCFO-1233zd (E), meaning that the amount of HCFO-1233zd(E) is greater than the amount of any HCFO-1233zd(Z) which may be present in the purified composition.

Various embodiments of the present process are described in further detail below with reference to FIGS. 1-10.

III. Schematics of the Present Process.

Referring to FIGS. 1-10, schematics of the present process are presented, showing the first, second, and third steps of the present process which may be performed under the general process conditions set forth above.

Referring to FIG. 1, a schematic of the first step of the present process is shown according to a first embodiment. In fluorination reactor 20, HCC-240fa is input via line 22 and fluorinated with hydrofluoric acid (HF) to produce HCFO-1233zd, and the products are conveyed via line 24 to distillation column 26 in which low boiling by-products, including HCFC-241fa and HF, are removed and conveyed to phase separator 28 via line 30. In phase separator 28, HF and HCFC-241fa separate via gravity, and the upper phase of HF is recycled back to fluorination reactor 20 via recycle line 32. The lower phase HCFC-241fa is removed from phase separator 28 via line 34 and then passes to the second step of the present process, described below. In this manner, the HCFC-241fa by product is separated, or isolated, from the main reaction by which HCFO-1233zd is produced by fluorination of HCC-240fa with HF.

Figure 2:
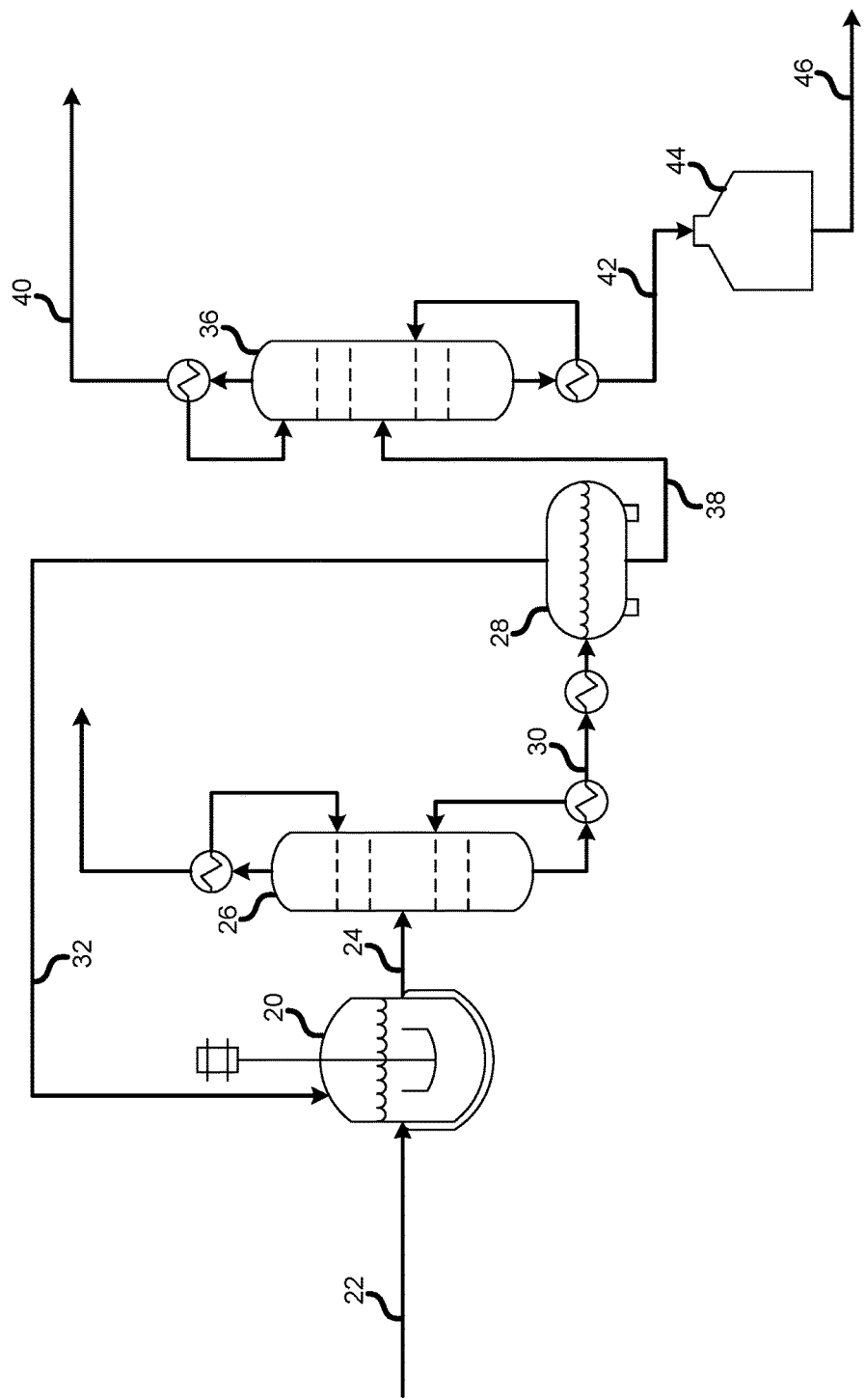
FIG. 2 is a schematic diagram of the first step of the present process according to a second embodiment.

Referring to FIG. 2, the first step of the present process is shown according to a second embodiment, wherein identical reference numerals are used to identify identical steps or components with respect to the prior embodiment described above. Referring to FIG. 2, separated HCFC-241fa is conveyed to a batch vacuum distillation column 36 via line 38, and low boiling by-products, such as HCFC-242fa, HCFO-1231zd, HCFO-1232zd, and HCFC-243fa, are removed from column 36 via overhead stream 40 and are separated and either recycled or disposed as waste. Purified HCFC-241fa is removed as bottoms stream 42 and conveyed to storage tank 44 and then via line 46 to the second step of the present process, described below.

Figure 3:
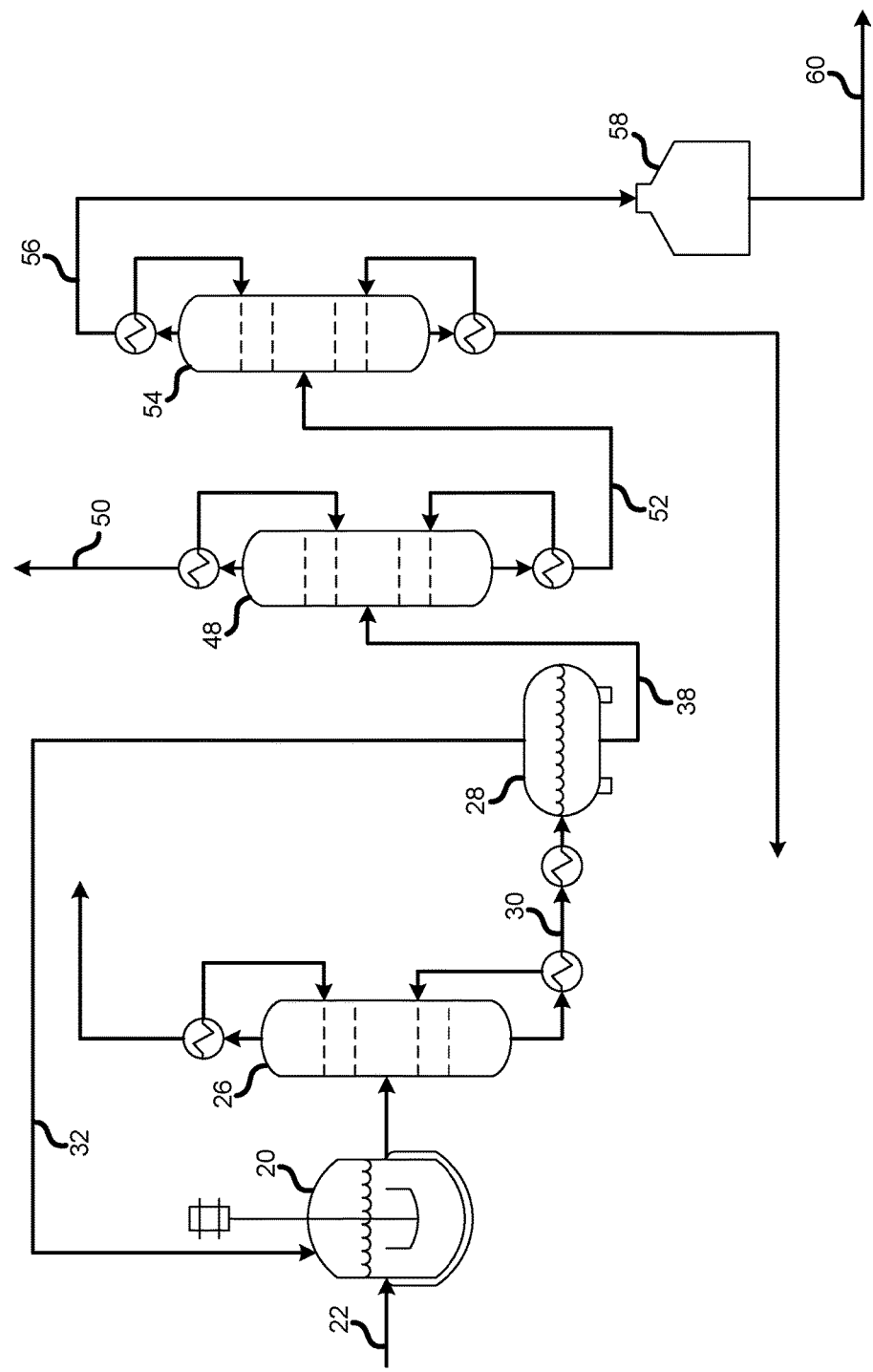
FIG. 3 is a schematic diagram of the first step of the present process according to a third embodiment.

Referring to FIG. 3, the first step of the present process is shown according to a third embodiment, wherein identical reference numerals are used to identify identical steps or components with respect to the prior embodiments described above. Referring to FIG. 3, separated HCFC-241fa is conveyed to a first continuous vacuum distillation column 48 where low boiling by-products, such as HCFC-242fa, HCFO-1231zd, HCFO-1232zd, and HCFC-243fa, are removed from column 48 via overhead stream 50 and are separated and either recycled or disposed as waste. Purified HCFC-241fa is removed as bottoms stream 52 and conveyed to a second continuous vacuum distillation column 54 where even more purified HCFC-241fa is removed via overhead stream 56, conveyed to storage tank 58, and then via line 60 to the second step of the present process, described below.

Figure 4:
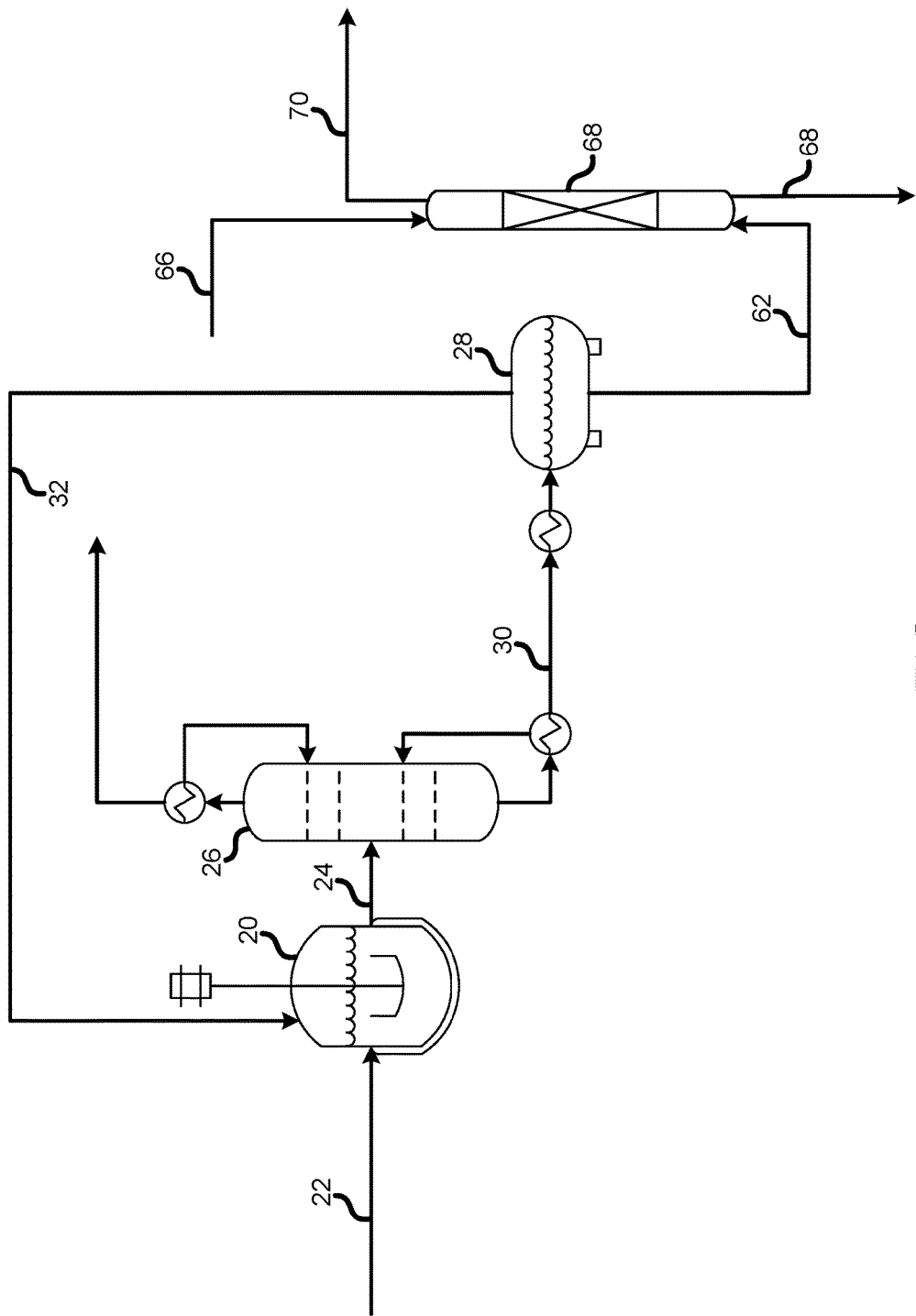
FIG. 4 is a schematic diagram of the first step of the present process according to a fourth embodiment.

Referring to FIG. 4, the first step of the present process is shown according to a fourth embodiment, wherein identical reference numerals are used to identify identical steps or components with respect to the prior embodiments described above. Referring to FIG. 4, separated HCFC-241fa is conveyed from phase separator 28 via line 62 and passes to HF scrubber 64 where the HCFC-241fa stream is contacted with water or a weak basic solution entering inlet line 66 to remove HF from the HCFC-241fa stream via outlet line 68. The purified HCFC-241fa is then conveyed via line 70 to the second step of the present process, described below.

Figure 5:
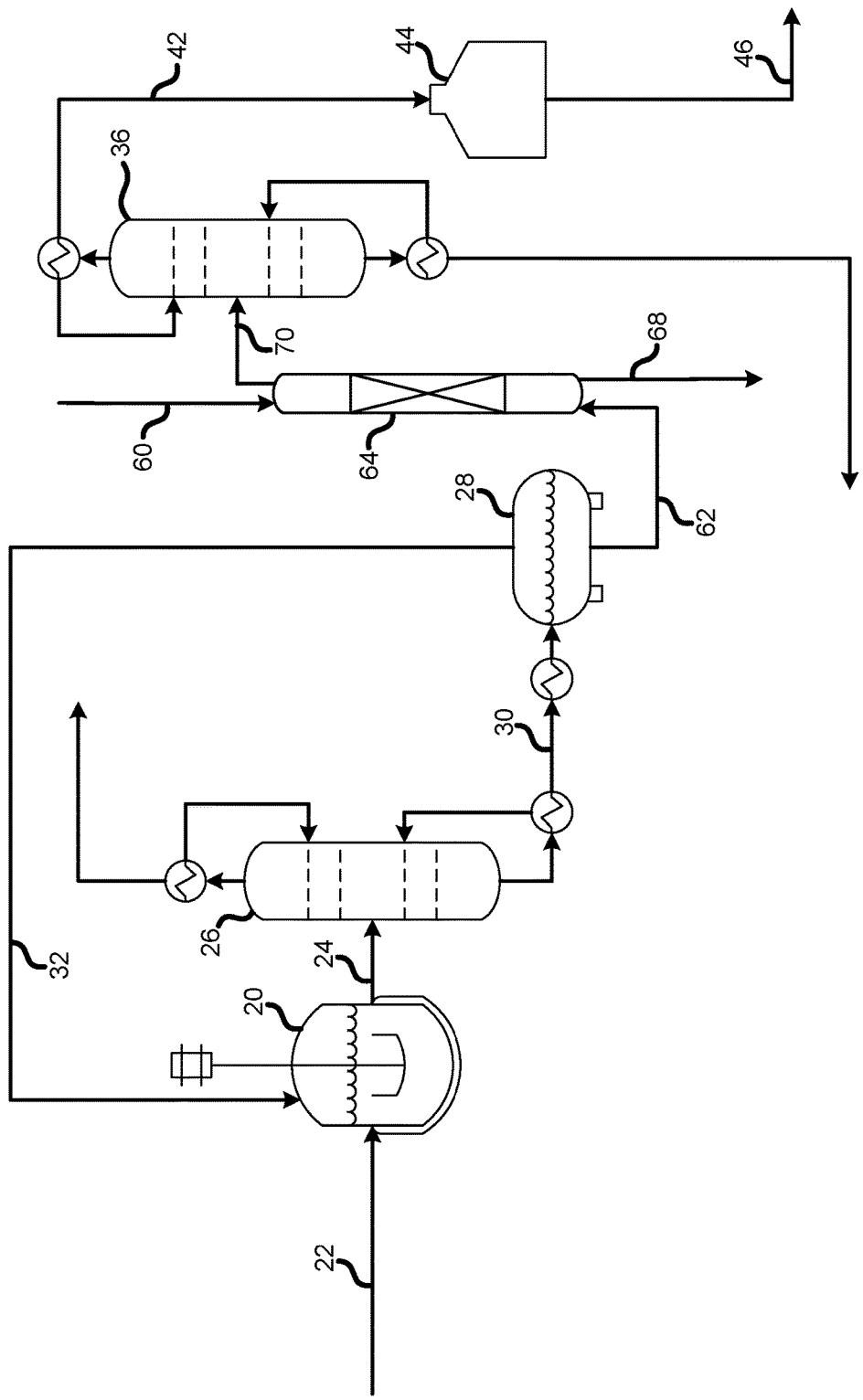
FIG. 5 is a schematic diagram of the first step of the present process according to a fifth embodiment.

Referring to FIG. 5, the first step of the present process is shown according to a fifth embodiment, wherein identical reference numerals are used to identify identical steps or components with respect to the prior embodiments described above. Referring to FIG. 5, the processes of FIGS. 2 and 4 described above are combined such that the separated HCFC-241fa is first contacted with a scrubbing solution in HF scrubber 64 to remove HF, and is subsequently processed in a batch vacuum distillation column 36 to remove low boiling by-products prior to being recovered in storage tank 44 and then conveyed to the second step of the present process via line 46.

Figure 6:
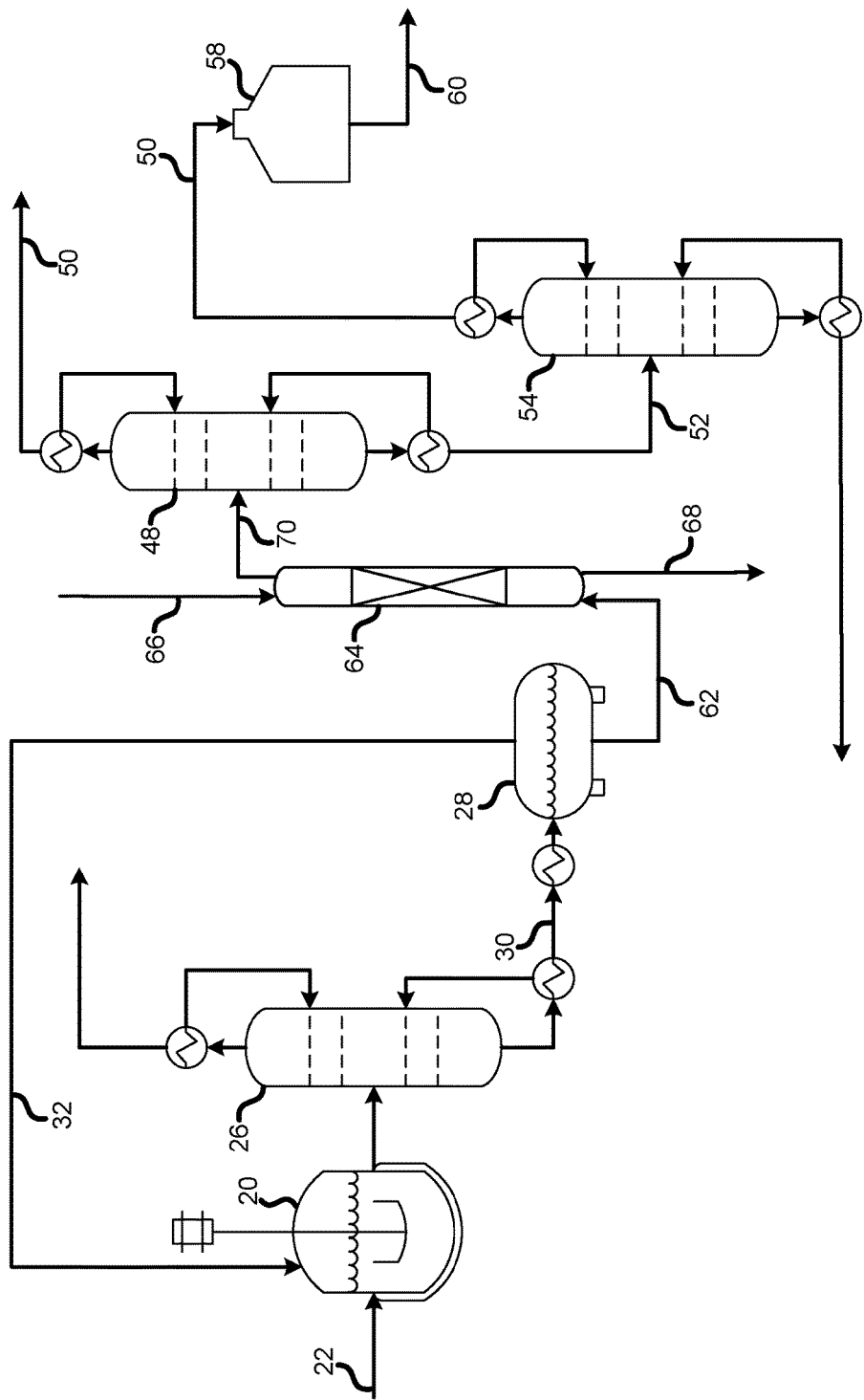
FIG. 6 is a schematic diagram of the first step of the present process according to a sixth embodiment.

Referring to FIG. 6, the first step of the present process is shown according to a sixth embodiment, wherein identical reference numerals are used to identify identical steps or components with respect to the prior embodiments described above. Referring to FIG. 6, the processes of FIGS. 3 and 4 described above are combined such that the separated HCFC-241fa is first contacted with a scrubbing solution in HF scrubber 64 to remove HF, and is subsequently processed in first and second continuous distillation columns 48 and 54 to remove low boiling by-products prior to being recovered in storage tank 58 and then conveyed to the second step of the present process via line 60.

Figure 7:
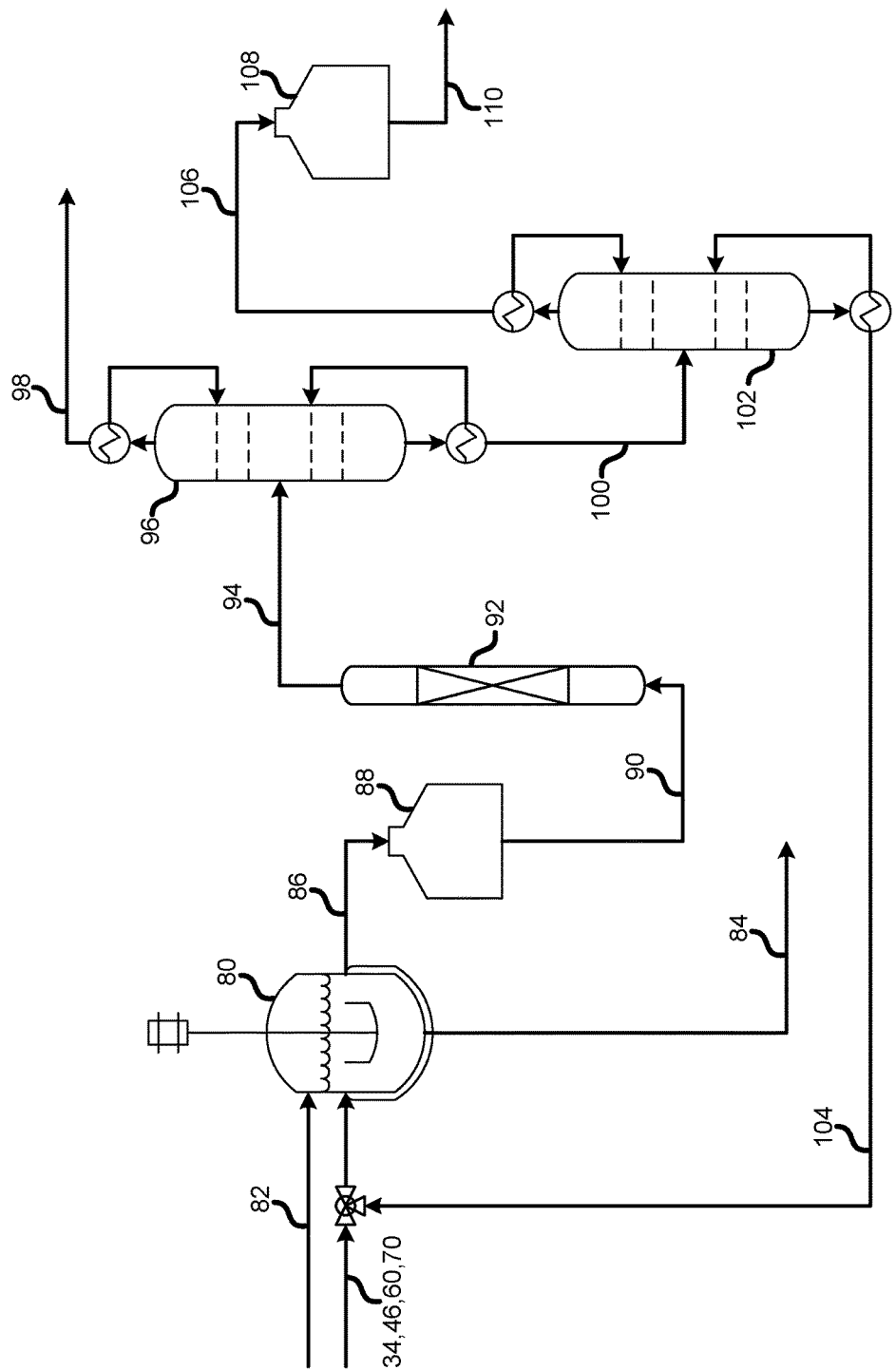
FIG. 7 is a schematic diagram of the second step of the present process according to a first embodiment.

Referring to FIG. 7, a schematic of the second step of the present process is shown according to a first embodiment. Referring to FIG. 7, purified HCFC-241fa from the first step of the present process is conveyed to a dehydrochlorination reactor 80 in which HCFC-241fa is dehydrochlorinated to HCFO-1231zd in the presence of a basic solution, as described above, which may enter reactor 80 via line 82, with spent basic solution exiting reactor 80 via line 84. The crude HCFO-1231zd is removed from reactor 80 via line 86 and is conveyed to storage tank 88. Thereafter, the crude HCFO-1231zd is conveyed via line 90 to drying column 92, which includes a suitable desiccant for removing moisture. Thereafter, the dried HCFO-1231zd is conveyed via line 94 to a first continuous vacuum distillation column 96 in which low boiling by-products are removed via overhead stream 98 to a collection vessel or waste disposal. The purified HCFO-1231zd is removed via bottom stream 100 and passes to a second continuous vacuum distillation column 102 in which by-products, such as unreacted HCFC-241fa and other high boiling by-products are removed via bottoms stream 104 and recycled back to dehydrochlorination reactor 80. The purified HCFO-1231zd is removed via overhead stream 106 and may be collected in storage tank 108 before being conveyed to the third step of the present process via line 110.

Figure 8:
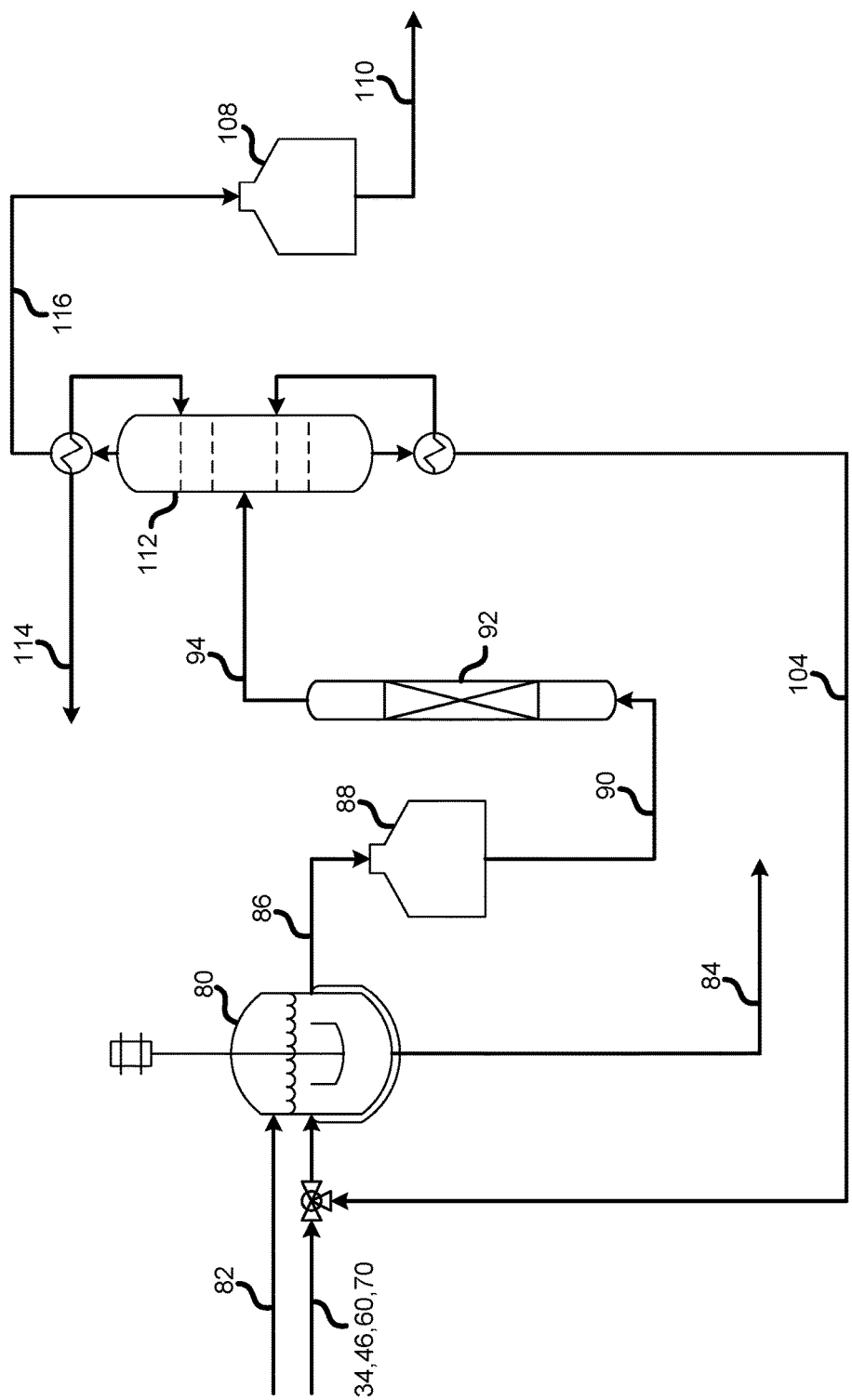
FIG. 8 is a schematic diagram of the second step of the present process according to a second embodiment.

Referring to FIG. 8, a schematic of the second step of the present process is shown according to a second embodiment, wherein identical reference numerals are used to identify identical steps or components with respect to the prior embodiment described above. Referring to FIG. 8, the dried HCFO-1231zd is conveyed to a batch vacuum distillation column 112 in which by-products, such as unreacted HCFC-241fa and other high boiling by-products, are removed via bottoms stream 104 and recycled back to dehydrochlorination reactor 80. Low boiling by-products are removed via overhead stream 114 and are conveyed to a collection vessel or waste disposal. Purified HCFO-1231zd is conveyed from column 112 via line 116 and may be collected in storage tank 108 before being conveyed to the third step of the present process via line 110.

Figure 9:
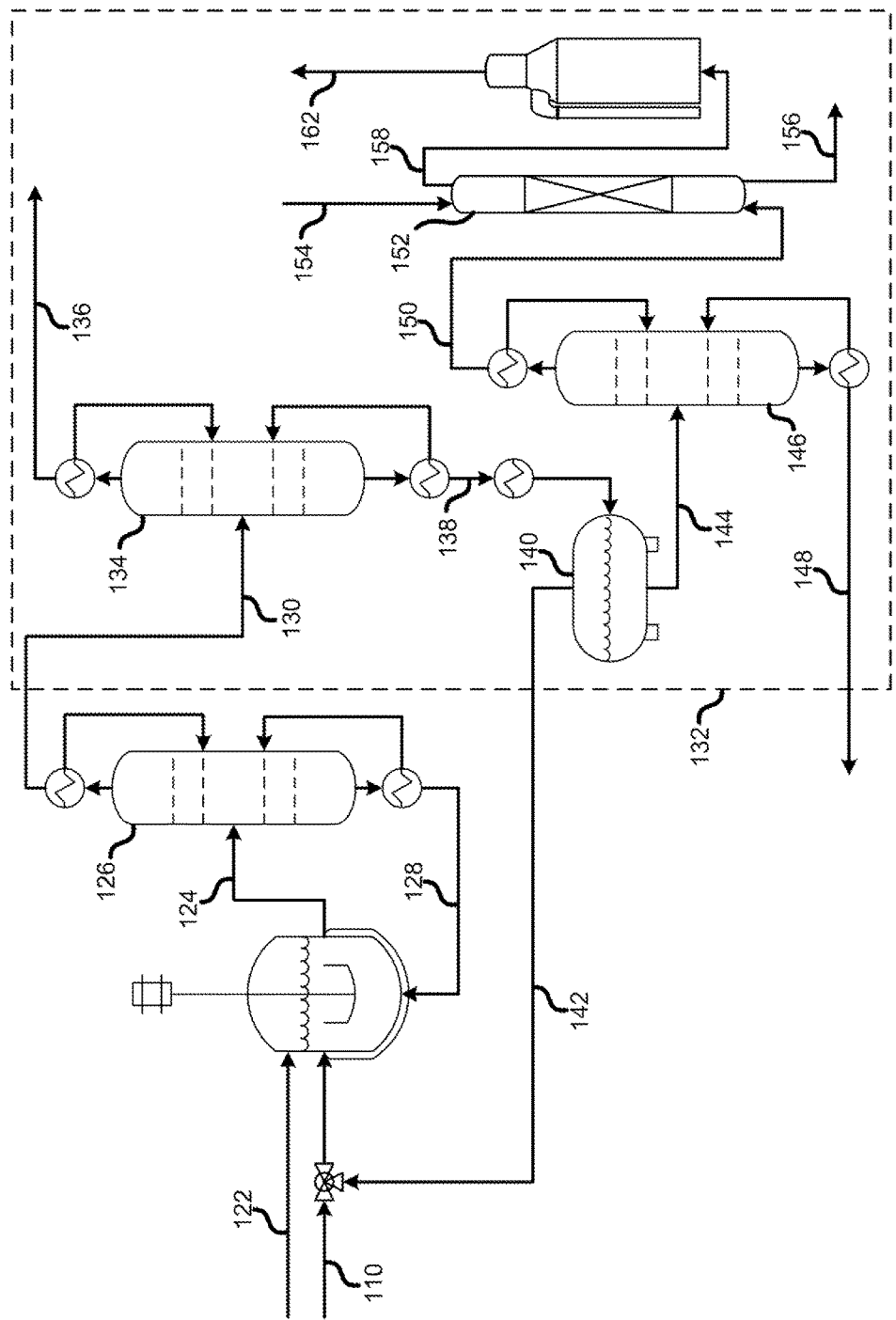
FIG. 9 is a schematic diagram of a first portion of the third step of the present process.
Figure 10:
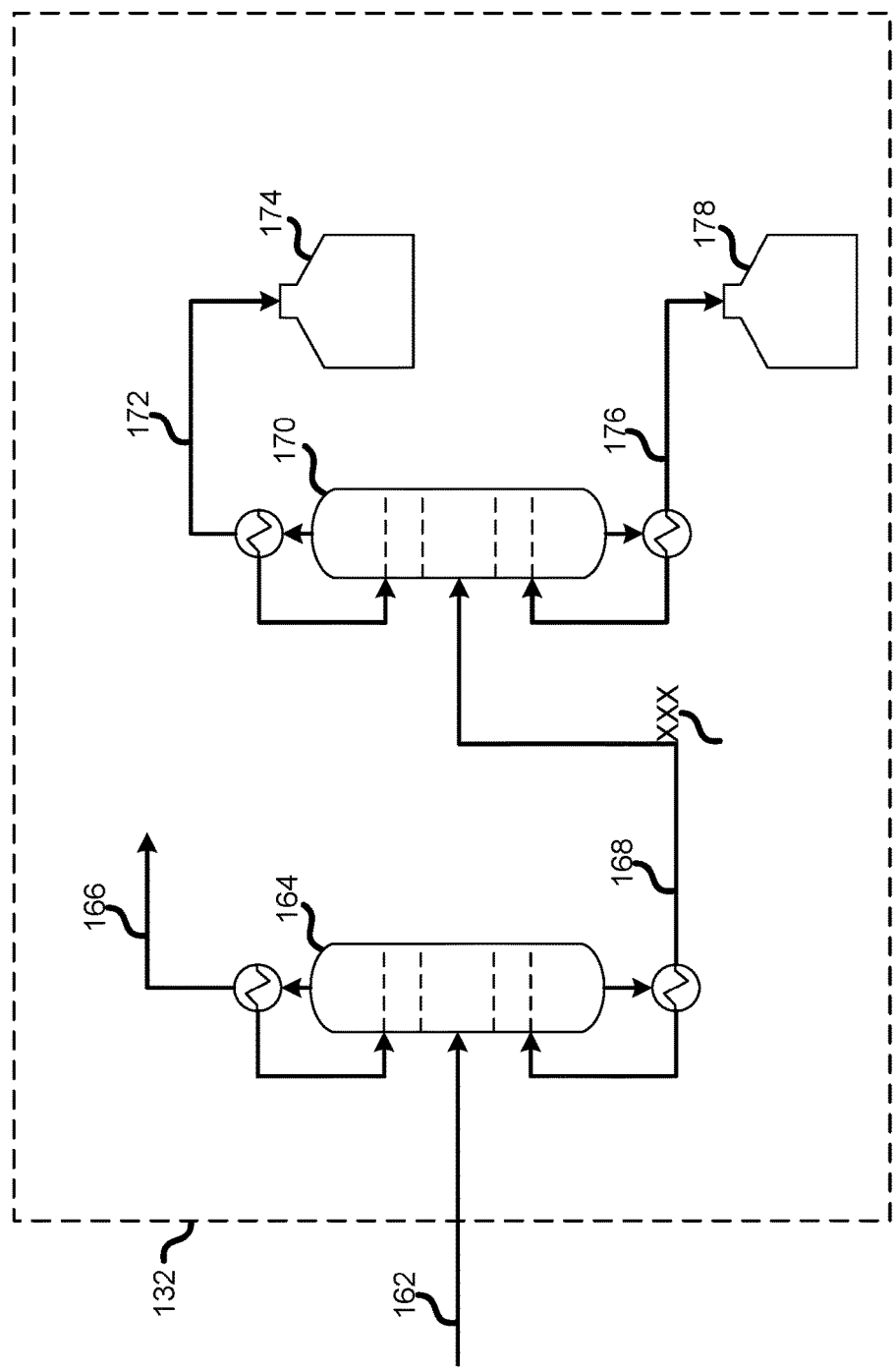
FIG. 10 is a schematic diagram of a second portion of the third step of the present process.

Referring to FIGS. 9 and 10, schematics of the third step of the present process are shown. Referring first to FIG. 9, purified HCFO-1231zd from the second step of the present process is conveyed to fluorination reactor 120 via line 110, along with a supply of HF via line 122, and crude HCFO-1233zd and by-products are conveyed via line 124 to recycle distillation column 126. High boiling by-products, such as unreacted HCFO-1231zd, any HCFO-1232zd intermediate which may be formed, and HF are separated via bottoms stream 128 and recycled back to reactor 20. Crude HCFO-1233zd is separated via overhead stream 130 to an HCl recovery, organic/HF recycle, and HCFO-1233zd purification stage 132.

In stage 132, a first distillation column 134 is used to separate HF as overhead stream 136, which may be isolated as a co-product, for example. HCFO-1233zd in bottoms stream 138 is conveyed to phase separator 140, where HF and HCFO-1233zd separate via gravity, with the separated upper phase HF conveyed from phase separator 140 via recycle line 142 back to fluorination reactor 120, or alternatively, merged into HF input stream 122. The separated lower phase HCFO-1233zd is conveyed from phase separator 140 via line 144 to distillation column 146, wherein high boiling by-products are separated via bottoms stream 148 to a collection vessel or waste disposal, for example.

HCFO-1233zd is removed via overhead stream 150 and conveyed to a scrubber column 152, in which water or a weak basic solution is conveyed into column 152 via inlet 154 to remove any residual HF as water or spent basic solution via outlet 156. The scrubbed HCFO-1233zd is then conveyed via line 158 to drying column 160 to remove any residual moisture using a desiccant, for example, and the dried HCFO-1233zd is then conveyed via line 162 to the further steps shown in FIG. 10.

Referring to FIG. 10, dried HCFO-1233zd is conveyed to lights distillation column 164 via line 162, where low boiling by-products are separated via overhead stream 166 and may be collected in a collection vessel or waste disposal. HCFO-1233zd(E) is separated via bottoms stream 168 and conveyed to product distillation column 170, where the purified HCFO-1233zd(E) is separated via overhead stream 172 and collected within collection container 174, and high boiling co-products, such as HCFO-1233zd(Z), which is typically a majority by-product, HCFC-244fa as a next most abundant by-product, a minor amount of HCFC-243fa, and very small amounts of other by-products, are separated via bottoms stream 176 and may be collected within collection container 178.

EXAMPLES

Example 1

Synthesis of HCFC-241fa Via
HCFC-240fa+HF→HCFC-241fa+HCl Reaction

A total of 10 batch reactions were completed in a 1 gallon autoclave. Reactions were performed at temperatures between 110-120° C. A total of about 4300 grams of 64 wt. % pure HCFC-241fa were collected after separating acid from organic and drying. Major impurity in the HCFC-241fa crude product was HCFC-240fa (about 25 wt. %) and HCFO-1233zd(E) (about 6 wt. %). In total, about 1400 grams of greater than 99 wt. % HCFC-241fa were recovered using a glass distillation column running at atmospheric pressure. Observed boiling point of HCFC-241fa at atmospheric pressure was 142-145° C.

Example 2

Recovery of HCFC-241fa from a Mixture of
Anhydrous Hydrogen Fluoride and HCFC-241fa by
Density Difference Using a Phase Separation
Technique 15.4 grams of the greater than 99.8 GC area % purity HCFC-241fa produced in Example 1 was added to 12.9 grams of anhydrous HF in a perfluoroalkoxy (PFA) copolymer sample container. The container was mixed by shaking, and was then placed in wet ice and allowed to settle. The HF and organic phases were not miscible as two distinct phases were present. The bottom phase contained HCFC-241fa and was sampled and analyzed by ion chromatography (IC) to measure HF content, and was found to contain 1.2 wt. % HF.

Example 3

Conversion of HCFC-241fa to HCFO-1231zd 1500 grams of HCFC-241fa with a purity of greater than 98 wt. % was added to a 3 L round bottom flask equipped with a glass mixer. 1 liter of 7.5 wt. % KOH solution was added to the HCFC-241fa and the mixer was turned on at ambient temperature at 20-21° C. The progress of the reaction was monitored by taking a sample of the organic liquid and analyzing with a gas chromatograph. The spent KOH solution was decanted and replaced with fresh 7.5 wt. % KOH solution whenever the progress of the reaction stalled (no additional HCFC-241fa conversion was observed). When less than 10 wt. % HCFC-241fa remained, the organic phase was recovered using a separatory funnel, washed with water to remove any salts that may have dissolved in the organic phase, and then dried with calcium sulfate. 1245 grams of organic phase was recovered, giving a 97.8 wt. % mass balance. Gas chromatography (GC) results indicated that both dehydrochlorination and dehydrofluorination reactions occurred, producing both HCFO-1231zd-cis and -trans isomers as a dehydrochlorination product and tetrachloropropene as a dehydrofluorination product. The selectivity to the HCFO-1231zd isomers was 83.8 mole %, the selectivity to tetrachloropropene 12.5 mole %, and the balance (3.7 mole %) was to other products.

Example 4

Separation of HCFO-1231zd

In this Example, 100 grams of greater than 99.6 GC area % purity HCFO-1231zd was separated via vacuum distillation from the crude HCFO-1231zd product of Example 3.

Example 5

Production of HCFO-1233zd

In this Example, the uncatalyzed chemical reaction for forming HCFO-1233zd(E) was further studied. In particular, the theory that starting with an unsaturated hydrochlorofluoroolefin (HCFO) such as HCFO-1231zd, as opposed to the saturated HCC-240fa or HCFC-241fa would be more selective to 1233zd(E) via a much faster reaction (higher conversion for a given set of operating conditions) was tested. Several batch reaction experiments individually starting with the foregoing different organic feed stocks were tested for the purpose of comparing conversion and selectivity to HCFO-1233zd(E) using an identical series of operating conditions for each of the feed stocks.

Reactions for all three feed stocks were run at 140° C. with a 1 hour hold time and 130° C. with a 3 hour hold time. Batch reaction experiments using HCFC-241fa and HCFO-1231zd only were run at 130° C. with a 1 hour hold times. All experiments used similar HF to organic mole ratios of about 17:1. These results are shown in FIGS. 11-13 and summarized below.

At all operating conditions the conversion of HCFO-1231zd was equal to or greater than 99.6% and the selectivity to HCFO-1233zd(E) was between 87.5 and 90%. The conversion of HCC-240fa was about 99.5%, but the selectivity to HCFO-1233zd(E) ranged from only 66.3% to 77.0% (respectively for the 140° C. and 130° C. experiments). The conversion of HCFC2-41fa was 51.4%, 84.3%, and 51.8%, respectively, for the three experiments and the selectivity to HCFO-1233zd(E) was only 64.5%, 83.4%, and 72.7% for the three experiments.

These results indicate that starting with an HCFO-1231zd feedstock to produce HFCO-1233zd(E) via a non-catalytic liquid phase reaction is superior in terms of conversion and/or HCFO-1233zd(E) selectivity in comparison with the use of HCC-240fa or HCFC-241fa feedstocks.

As used herein, the phrase "within any range defined between any two of the foregoing values" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

While this disclosure has been described as relative to exemplary designs, the present disclosure may be further modified within the spirit and scope of this disclosure. Further, this application is intended to cover such departures from the present disclosure as come within known or customary practice in the art to which this disclosure pertains.

The invention claimed is:

1. A process for the production of 1-chloro-3,3,3-trifluoropropene (HCFO-1233zd), comprising the steps of:
   providing a reactant composition including 1,1,3,3-tetrachloro-1-fluoropropane (HCFC-241fa);
   dehydrochlorinating the HCFC-241fa in the presence of a basic solution to form 1,3,3-trichloro-3-fluoropropene (HCFO-1231zd); and
   fluorinating the HCFO-1231zd with hydrogen fluoride (HF) to produce HCFO-1233zd.

2. The process of claim 1 wherein following said fluorinating step, the HCFO-1233zd produced is predominantly HCFO-1233zd(E).

3. The process of claim 1, wherein said dehydrochlorinating step is performed at a temperature between 0° C. and 100° C.

4. The process of claim 1, wherein said fluorinating step is performed at a temperature between 80° C. and 150° C.

5. The process of claim 1, wherein said fluorinating step is performed in the absence of a catalyst.

6. The process of claim 1, wherein the reactant composition further includes hydrogen fluoride (HF) and said process further includes the additional step, after said providing step and prior to said dehydrochlorinating step, of separating HF from the reactant composition.

7. The process of claim 1, further comprising the additional step, after said dehydrochlorinating step and prior to said fluorinating step, of drying the HCFO-1231zd.

8. The process of claim 1, wherein the basic solution in said dehydrochlorinating step is selected from the group consisting of potassium hydroxide (KOH), sodium hydroxide (NaOH), and calcium hydroxide (CaOH).

9. A process for the production of 1-chloro-3,3,3-trifluoropropene (HCFO-1233zd), comprising the steps of:
   fluorinating 1,1,1,3,3-pentachloropropane (HCC-240fa) with hydrofluoric acid (HF) to produce a product stream including HCFO-1233zd and 1,1,3,3-tetrachloro-1-fluoropropane (HCFC-241fa);
   separating HCFC-241fa from the product stream;
   dehydrochlorinating the HCFC-241fa in a liquid phase in the presence of a basic solution to form 1,3,3-trichloro-3-fluoropropene (HCFO-1231zd); and
   fluorinating the HCFO-1231zd with hydrogen fluoride (HF) to produce HCFO-1233zd.

10. The process of claim 9, wherein said first fluorinating step is performed at a reaction temperature between 120° C. and 140° C. and at a reaction pressure of between 230 psig and 400 psig.

11. The process of claim 9 wherein, following said second fluorinating step, the HCFO-1233zd produced is predominantly HCFO-1233zd(E).

12. The process of claim 9, wherein said dehydrochlorinating step is performed at a temperature between 0° C. and 100° C.

13. The process of claim 9, wherein said second fluorinating step is performed at a temperature between 80° C. and 150° C.

14. The process of claim 9, wherein said second fluorinating step is performed in the absence of a catalyst.

15. The process of claim 9, wherein said process further includes an additional step, after said first fluorinating step and prior to said separating step, of separating HF from the product stream.

16. The process of claim 9, further comprising the additional step, after said dehydrochlorinating step and prior to said second fluorinating step, of drying the HCFO-1231zd.

17. The process of claim 9, further comprising the additional step, after said second fluorinating step, of recycling at least one of unreacted HCFO-1231zd and unreacted HF back to said first fluorinating step.

18. The process of claim 9, wherein said separating step is conducted via vacuum distillation.

19. The process of claim 9, wherein said separating step is conducted via distillation at a pressure between 10 torr and 5,200 torr.

* * * * *